United States Patent [19]

Gyure et al.

[11] Patent Number: 5,599,313

[45] Date of Patent: Feb. 4, 1997

[54] NEEDLE SHIELD ASSEMBLY HAVING SAFETY INDICATION FEATURES

[75] Inventors: Sandor Gyure, West Orange; Robert B. Odell, Franklin Lakes; Sandor Szabo, Elmwood Park, all of N.J.

[73] Assignee: Becton, Dickinson and Company, Franklin Lakes, N.J.

[21] Appl. No.: 384,302

[22] Filed: Feb. 3, 1995

[51] Int. Cl.⁶ .................................................. A61M 5/32
[52] U.S. Cl. ........................ 604/192; 604/111; 604/263
[58] Field of Search .................................. 604/111, 181, 604/187, 188, 192, 197, 198, 199, 263

[56] References Cited

U.S. PATENT DOCUMENTS

| | | |
|---|---|---|
| 3,658,061 | 4/1972 | Hall . |
| 4,664,259 | 5/1987 | Landis . |
| 4,747,836 | 5/1988 | Luther . |
| 4,838,871 | 6/1989 | Luther . |
| 4,872,552 | 10/1989 | Unger . |
| 4,886,503 | 12/1989 | Miller . |
| 4,909,792 | 3/1990 | Norelli . |
| 4,944,397 | 7/1990 | Miller . |
| 4,982,842 | 1/1991 | Hollister . |
| 5,055,102 | 10/1991 | Sitnik . |
| 5,116,325 | 5/1992 | Paterson . |
| 5,151,089 | 9/1992 | Kirk, III et al. . |
| 5,232,454 | 8/1993 | Hollister . |
| 5,312,366 | 5/1994 | Vailancourt ........................ 604/192 |
| 5,312,369 | 5/1994 | Arcusin et al. . |
| 5,338,310 | 8/1994 | Lewandowski ....................... 604/198 |
| 5,405,332 | 4/1995 | Opalek ................................. 604/263 |

*Primary Examiner*—Corrine M. McDermott
*Assistant Examiner*—N. Kent Gring
*Attorney, Agent, or Firm*—John L. Voellmicke

[57] ABSTRACT

A needle shield assembly of the present invention includes a needle cannula having a proximal end, a distal end and a lumen therethrough. A hub having a proximal end for connecting to a medical instrument and a distal end connected to the proximal end of the needle cannula is provided. A base member is connected to the hub. An elongate needle shield includes a proximal end hingedly connected to the base member, a distal end and a longitudinal axis therebetween. The needle shield includes a longitudinal opening therein. The needle shield is capable of rotating from a first position exposing at least the distal end the needle cannula and a second position wherein the needle cannula is within the longitudinal opening of the needle shield. A sleeve having a longitudinal slot is rotatably connected to the needle shield. The sleeve is capable of rotating about the needle shield to an open position where the longitudinal slot in the sleeve and the longitudinal opening in the needle shield are sufficiently aligned to allow passage of the needle cannula so that the needle shield can be rotated from the first position to the second position. The sleeve is rotatable about the needle shield, to a position which blocks the longitudinal opening of the needle shield. Color safety indicator means for visually indicating the sleeve is rotated to a position which blocks the longitudinal opening of the needle shield is provided.

17 Claims, 7 Drawing Sheets

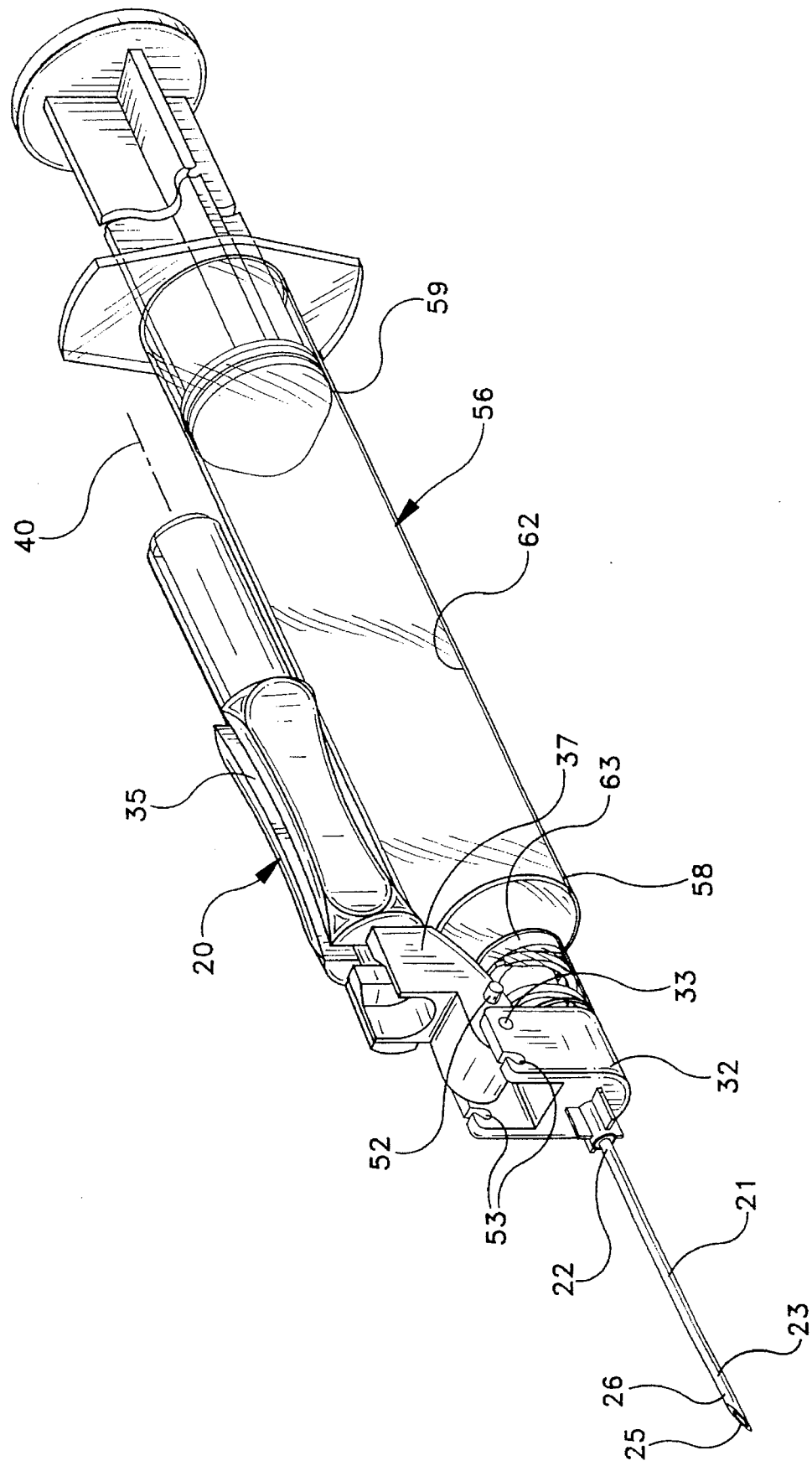

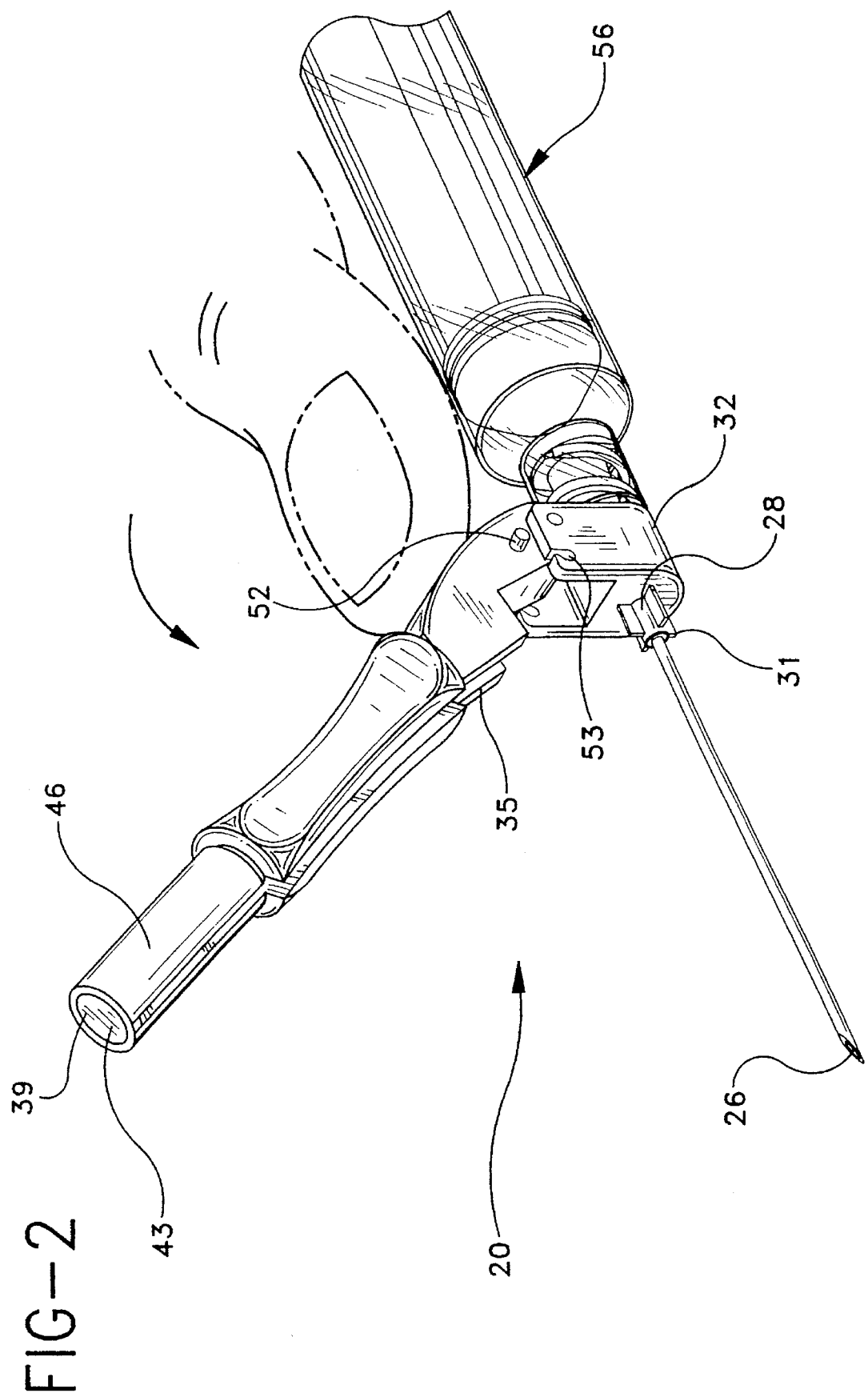

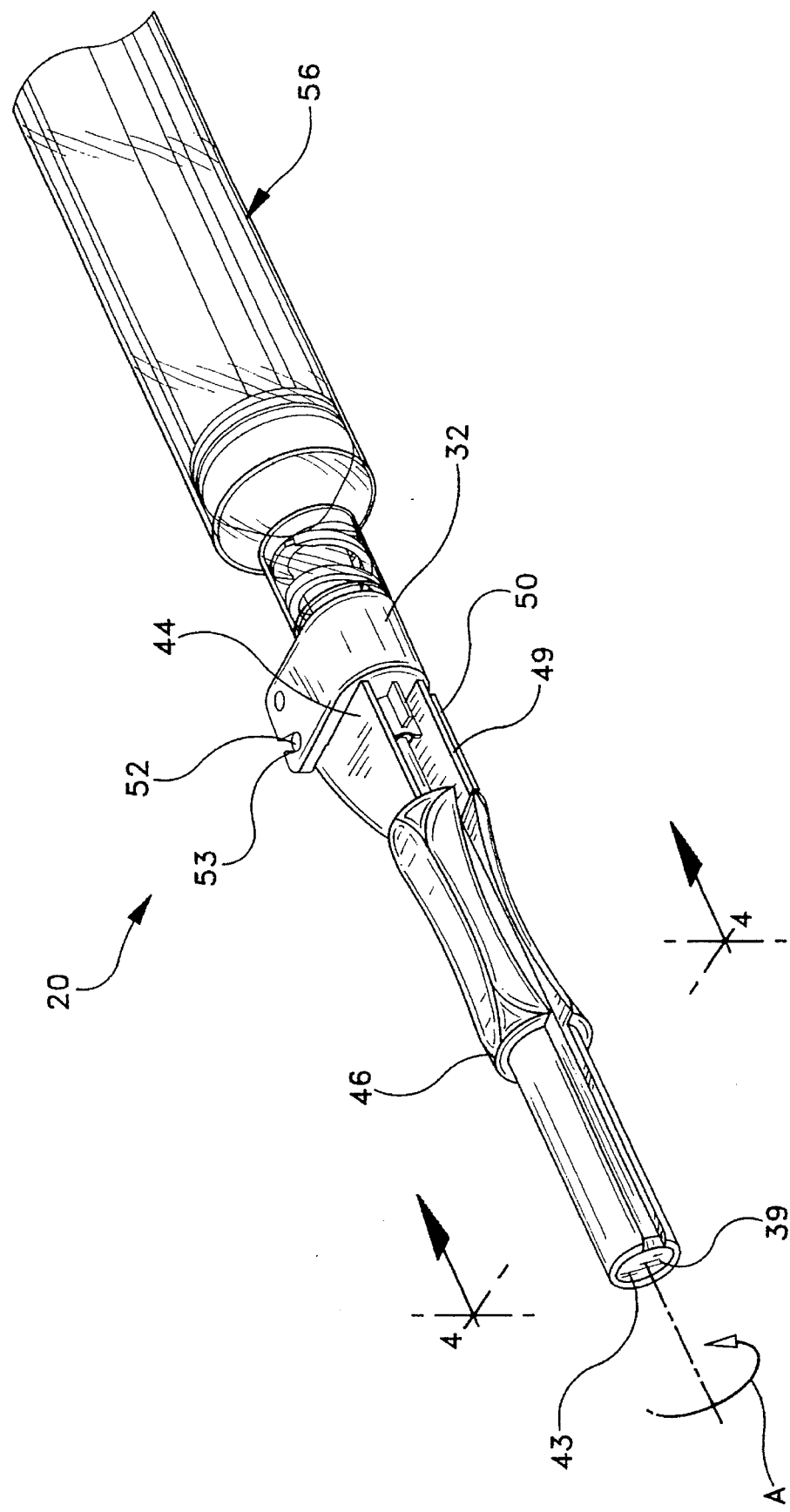

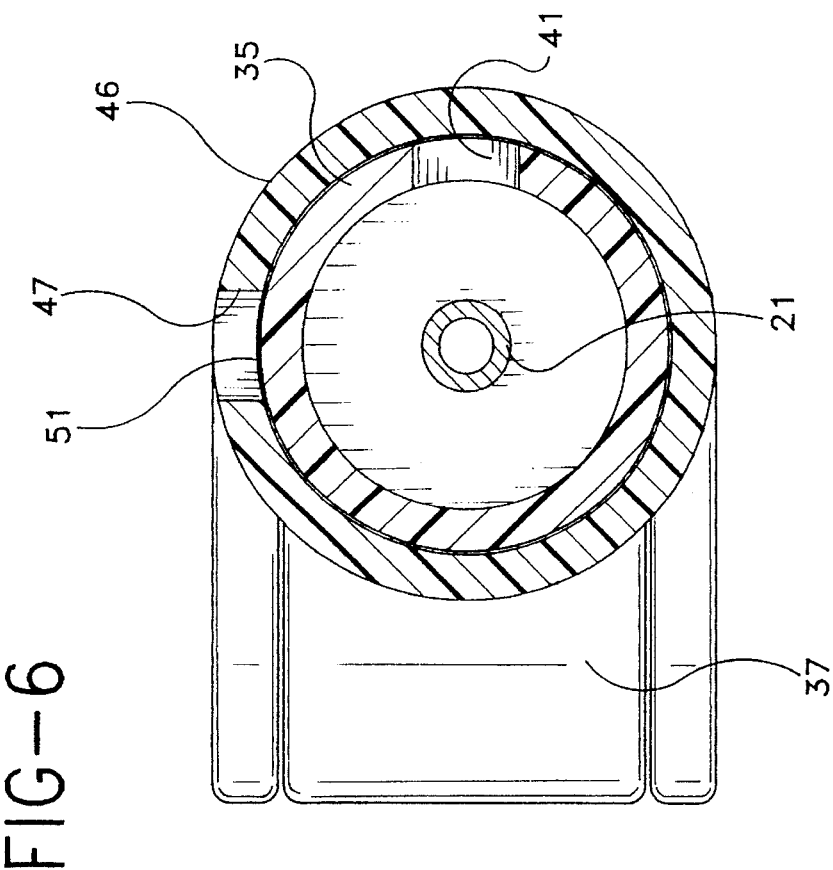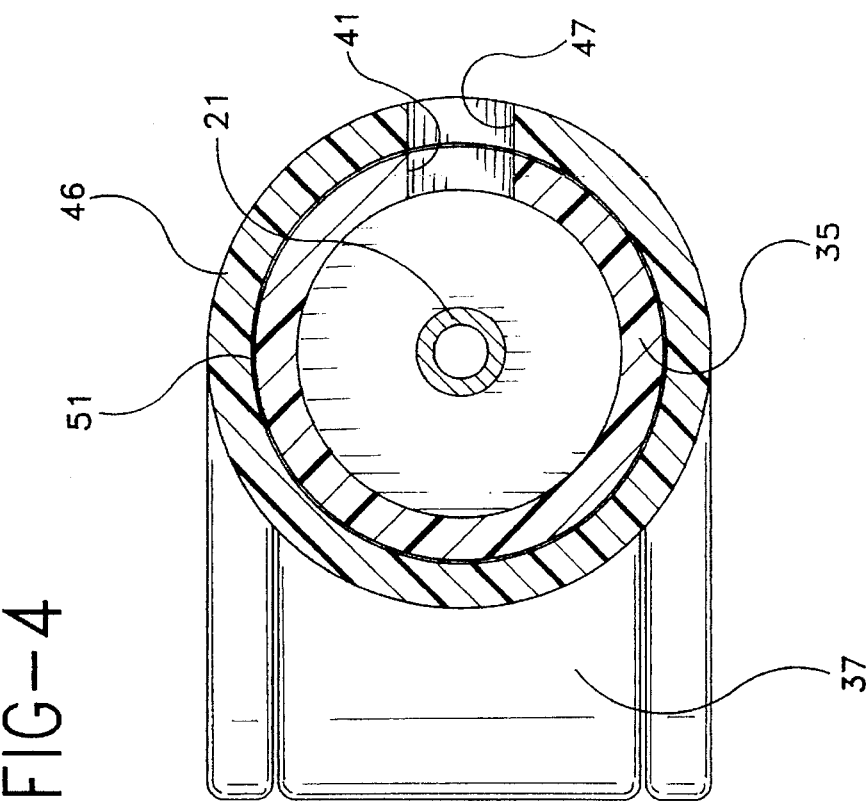

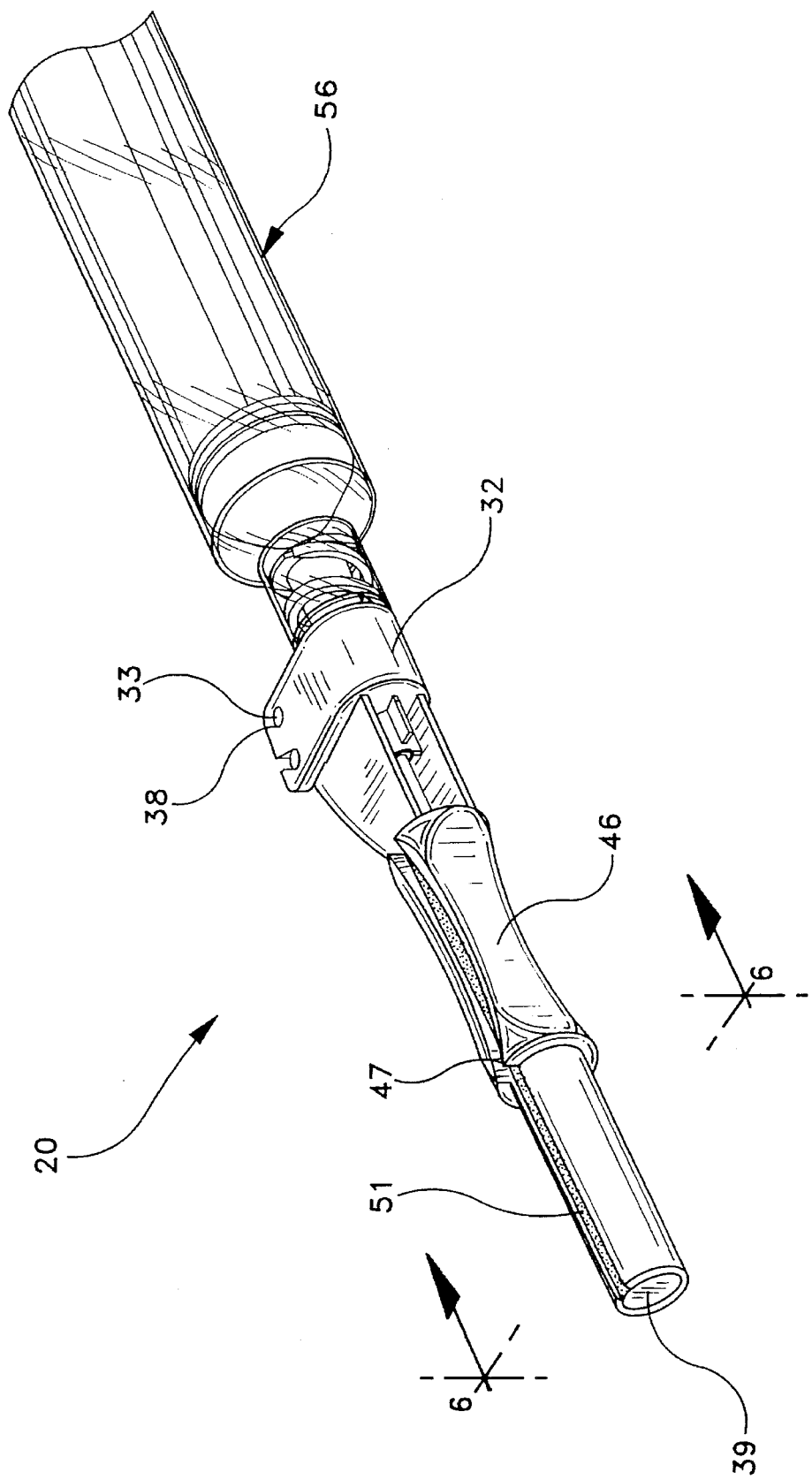

5,599,313

1

NEEDLE SHIELD ASSEMBLY HAVING SAFETY INDICATION FEATURES

FIELD OF THE INVENTION

The subject invention relates to needle shields for hypodermic needles, blood collection needles, catheter needles and other medical implements to help prevent accidental needle sticks.

DESCRIPTION OF THE PRIOR ART

Accidental needle sticks with a used needle cannula can transmit disease. As a result, most prior art needle cannulas have a safty shield. Some prior art shields define a rigid sleeve that can be telescoped in a proximal direction over the used needle cannula. This re-shielding procedure requires the healthcare worker to hold the needle cannula and the associated medical implement in one hand and the shield in the other. Many medical procedures require the application of pressure to the penetration site after the needle has been removed. Thus, healthcare workers often are unable to use both hands for shielding the needle cannula. In these situations, workers may merely deposit the used medical implement on a nearby surface with the intention of completing the shielding at a more convenient time. However, until the needle is shielded or properly disposed of it presents a potential danger to other people Some prior art hypodermic syringes include a shield telescoped around the needle cannula rather than around the syringe barrel This type of shield is advanced distally after the hypodermic syringe has been used. This prior art assembly with the shield telescoped on the needle hub requires a needle which is approximately twice as long as the needle required for the procedure because needle length is taken up by the telescoping elements before use. These devices too, unless spring loaded, require two hands for shielding.

Some prior art safety shields have relied on coil springs coaxially positioned around the needle cannula to automatically move the shield. The shield may be locked in the proximal position with the coil spring compressed. Unlocking the shield causes the coil spring to urge the shield distally into the shielded position. However, it is generally undesirable to provide an apparatus which is usually made of thermoplastic components to be stored for a considerable period of time under the stress of a compressed coil spring. The stored energy can cause the plastic parts to deform, and may alter the performance of the shield.

Many prior art self-contained needle shield assemblies lock permanently in place once the needle cannula is shielded for the first time. Accordingly, once the syringe needle is used for filling through a medication vial having a pierceable septum, it must be transported to the injection site unshielded. Other prior art devices can be unshielded after they are shielded, however, there is no clear indication to the user if the shield is securely locked in the needle shielding position or if the needle is shielded and the shield is not locked and can be easily displaced to an unshielded position and possibly cause a needle stick injury.

Although the prior art provides many improved needle shield devices, there is still a need for a self-contained needle shield assembly wherein the shield can be positioned using a one-handed procedure and the shield can be selectively locked, to prevent further use, or intentionally unlocked to allow a second use of the needle such as when the needle is used both for filling the syringe and for delivering the medication. There is also a need for such a self-contained shielded needle cannula that provides a clear indication to the user that the shield is safely and securely locked over the cannula and that the needle assembly can be disposed of without further risk of needle sticks.

SUMMARY OF THE INVENTION

A needle shield assembly of the present invention includes a needle cannula having a proximal end, a distal end and a lumen therethrough. A hub having a proximal end connecting to a medical instrument and a distal end connected to the proximal end of the needle cannula is provided. A base member is connected to the hub. An elongate needle shield includes a proximal end hingedly connected to the base member, a distal end and a longitudinal axis therebetween. The needle shield includes a longitudinal opening therein the needle shield is capable of rotating from a first position exposing at least the distal end of the needle cannula and a second position wherein the needle cannula is within the longitudinal opening of the needle shield. A sleeve having a longitudinal slot is rotatably connected to the needle shield. The sleeve is capable of rotating about the needle shield to an open position where the longitudinal slot in the sleeve and the longitudinal opening in the needle shield are sufficiently aligned to allow passage of the needle cannula so that the needle shield can be rotated from the first position to the second position and back to the first position, if desired. The sleeve is rotatable about the needle shield, to a position which blocks the longitudinal opening of the needle shield. Color safety indicator means for visually indicating the sleeve is rotated to a position which blocks the longitudinal opening of the needle shield is provided.

BRIEF DESCRIPTION OF THE DRAWINGS

FIG. 1 is a perspective view of the needle shield assembly of the present invention connected to a hypodermic syringe.

FIG. 2 is a perspective view of the needle shield assembly of FIG. 1 illustrating the needle shield being single-handedly moved toward a needle shielding position.

FIG. 3 is a perspective view of the needle shield assembly of FIG. 1 in the closed, unlocked needle shielding position.

FIG. 4 is a cross-sectional view of the needle shield assembly of FIG. 3 taken along line 4—4.

FIG. 5 is a perspective view of the needle shield assembly of FIG. 4 with the needle shield sleeve rotated to the locked position and the safety indicator exposed.

FIG. 6 is a cross-sectional view of the needle shield assembly of FIG. 5 taken along lines 6—6.

DETAILED DESCRIPTION

Figure 7:
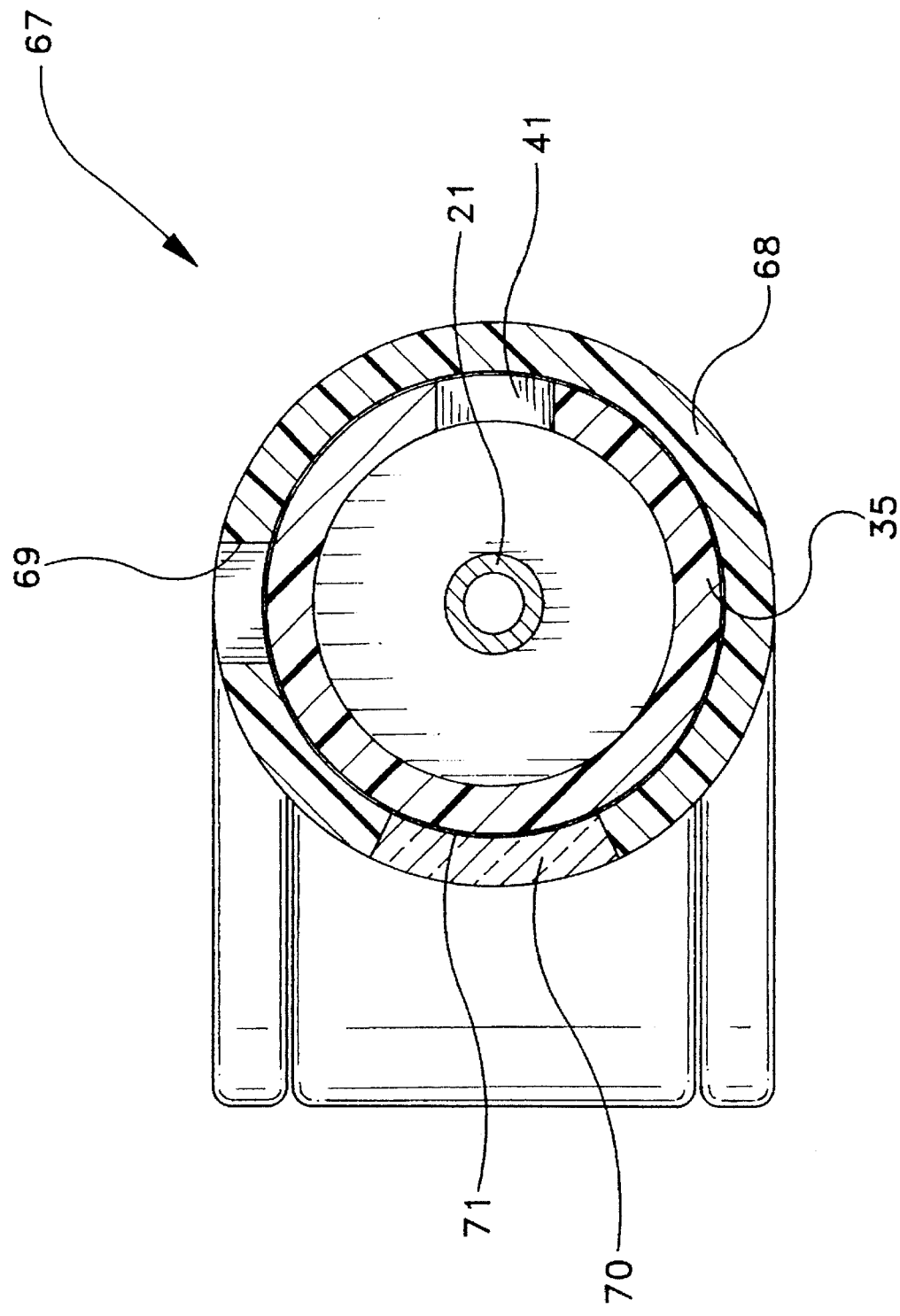
FIG. 7 is a cross-sectional view of an alternative embodiment similar to the needle assembly of FIG. 6 but having a transparent window to view the color segment

While this invention is satisfied by embodiments in many different forms, there are shown in the drawings and will be herein described in detail preferred embodiments of the invention with the understanding that the present disclosure is to be considered exemplary of the principles of the invention and is not intended to limit the scope of the invention to these embodiments illustrated. The scope of the invention will be measured by the appended claims and their equivalents.

Adverting to FIGS. 1–6, a needle shield assembly having safety indication features such as needle shield assembly 20 includes a needle cannula 21 having a proximal end 22, a distal end 23 and a lumen 25 therethrough. In this embodiment, the distal end of the needle cannula includes a sharpened tip 26. A hub 28 includes a proximal end 29 and a distal end 31 connected to proximal end 22 of the needle cannula. A base member 32 is connected to the hub. There are many ways to join the base member to the hub such as through an interference fit, adhesives, ultrasonic welding and the like. It may be desirable in high volume production to integrally injection mold the hub and the base member as a one-piece unit thereby eliminating the assembly step.

An elongate needle shield 35 includes a proximal end 37 hingedly connected to base member 32. In this embodiment, the hinge connection is accomplished by hinge holes 34 in spaced parallel arms 33 of the base member wherein opposed circular hinge pins 38 on the elongate needle shield engage hinge holes 34 to allow the needle shield to rotate about an axis which is transverse to the longitudinal axis of the needle cannula. Elongate needle shield 35 also includes a distal end 39. A longitudinal axis 40 extends between the proximal and distal end of the needle shield. The needle shield includes longitudinal opening 41 which ends at the distal end of the needle shield at end wall 43. The longitudinal opening allows the needle shield to rotate about the base member from a first position exposing the distal end of the needle cannula to a second position wherein said needle cannula is within said longitudinal opening of the needle shield, as best illustrated in FIGS. 3 and 4. In this preferred embodiment the first position of the needle shield, exposing the distal end of the needle, is preferably at approximately 180° from the second position, as illustrated in FIG. 1. However, it is within the purview of this invention to have a first position at any angle between several degrees and 180° which exposes the distal end of the cannula for its intended purpose, such as, approximately 90° from the second position, so that in the first position the longitudinal axis of the needle shield is approximately perpendicular to the longitudinal axis of the needle cannula. However, the 180° first position is preferred because it is less obtrusive and less likely to interfere with the injection process.

A sleeve 46 having a longitudinal slot 47 is rotatably connected to needle shield 35. Sleeve 46 is capable of rotating from an open position wherein the longitudinal slot 47 and the longitudinal opening 41 are sufficiently aligned to allow the passage of the needle cannula so that the needle shield can be rotated from the first position to the second position, as best illustrated in FIG. 4. Sleeve 46 is rotatable to a position which blocks longitudinal opening 41 of the needle shield, as best illustrated in FIG. 6, so that the needle shield can be locked or secured trapping the needle cannula within the shield.

It is important that the user know when the longitudinal opening is blocked to prevent re-exposure of the sharp needle cannula and when the longitudinal opening is unobscured so that the needle shield can be rotated from the second needle covering position to the first needle exposing position.

In order to make the needle shield an effective barrier which will prevent accidental contact with the needle cannula it is desirable to have the longitudinal slot as narrow as possible. However, with a narrow slot it is sometimes difficult to visualize if the slot is open or shut. Accordingly, a safety indicator means is provided for visually indicating when sleeve 46 is rotated to a position which blocks longitudinal opening 41 of needle shield 35. In this preferred embodiment, the sleeve is mounted on the exterior of the needle shield and a color segment 51 is deposited on the exterior of the needle shield. The color segment can also be molded into the shield, such as by two-part molding, or the entire shield can be molded in color. It is preferred that color segment 51 be a bright color which is easily visualized from a short distance such as green, which usually indicates safety, or white, black or blue. Other colors are within the purview of the present invention. When the sleeve is rotated to cover longitudinal opening 41, as best illustrated in FIG. 6, longitudinal slot 47 is positioned over color segment 51 on the needle shield projecting to the user a bright colored longitudinal stripe which indicates that the needle cannula is securely contained within the needle shield and rotation of the needle shield will not re-expose the needle to the user. Also, the color indicating means indicates that if the user attempts to rotate the needle shield the needle will be bent while still remaining trapped within the needle shield. Accordingly, a user who intends to re-expose the needle cannula will rotated the sleeve to the position which exposes longitudinal opening 41 so that the needle shield can be safety rotated to re-expose the needle without bending or damaging the needle.

It is convenient to use the longitudinal slot in the sleeve for allowing the needle shield to rotate and also for exposing the color segment. However, another aperture can be placed in the sleeve for the same purpose. Also, the sleeve can be manufactured to have a transparent segment so that when the sleeve is rotated to the position which blocks the longitudinal opening of the needle shield the transparent section of the sleeve will be over the color segment. The embodiment shown in FIGS. 1–6 is merely preferred because of its simplicity and ease of manufacture. It is also within the purview of the present invention to have the sleeve inside the needle shield so that the safety indicator would have to be on the sleeve and the aperture or transparent section would have to be on the needle shield. This embodiment is not preferred because the most practical way to rotate the shield would be having the sleeve project beyond the distal end of the needle, and it is preferred to keep the operator's fingers away from the distal end of the needle.

It is preferred to have a means for limiting the rotational movement of the sleeve with respect to the needle shield. In the preferred embodiment means for limiting rotational movement includes a projection 50 on proximal end 45 of sleeve 46 and a protuberance 44 on proximal end 37 of needle shield 35. When the sleeve is rotated in a counterclockwise direction, indicated as A in FIG. 3, with respect to the needle shield it will rotate from the position of FIGS. 3 and 4 to the position of FIGS. 5 and 6. At this point, projection 50 will contact protuberance 44, as best illustrated in FIG. 5, preventing further counterclockwise movement of the sleeve. At this point, the color segment is conveniently located within the longitudinal slot of the sleeve and rotation cannot proceed too far, and the user is not forced to rotate the sleeve back and forth to find the safety indicator means. Accordingly, rotating the sleeve to the position of safe containment of the needle cannula is accompanied by the tactile sensation of the projection abutting against the protuberance, and the visual sensation of observing the color segment. At this point the user knows that the needle is safety shielded and cannot be accidentally reexposed. It is also possible, and desirable, to configure the projection and the protuberance so that there is a reversible snap-fit type engagement which will provide a tactile sensation when the projection and the protuberance engage and also provide a resisting force which will require the user to apply a more deliberate force to re-expose the longitudinal opening of the needle shield. This tactile sensation could also be provided by a projection on the sleeve or needle shield and a complimentary cavity in the needle shield or sleeve so that at the position where the longitudinal opening of the needle shield is covered and the color segment is visible, the projection falls into the cavity making an audible sound. Also, a more aggressively configured projection and cavity could be used to produce a needle shield wherein the sleeve is permanently locked the first time it is rotated to a position in which it covers the longitudinal opening of the needle shield and exposes the color segment. In some applications, this structure is desirable to avoid a second, unwanted, use of the needle.

It is desirable to have the needle shield not freely rotatable about the base member when it is in the second needle shielding position so that the needle shield does not inadvertently or accidentally move while the user is rotating the sleeve to block the longitudinal opening of the needle shield. Accordingly, it is desirable to releasably retain the needle shield in the second needle protecting position so that a certain amount of force is required to rotate the needle shield out of this position. In this embodiment, means for releasably retaining the needle shield in the second position comprises a projection 52 on needle shield 35 and a recess 53 on base member 32 which is sized and shaped to frictionally engage the projection on the base member when the needle shield is rotated into the second position. In the preferred embodiment, recess 53 is narrower at its opening so that the projection snaps into the recess to releasably hold the needle shield in the second position. The retention force is intended to be minimal, to avoid accidental and not intentional rotation of the needle shield. There are numerous ways to releasably retain the needle shield in the second position and the projection and slot structure illustrated is merely representative of these many ways. The projection and the slot can be reversed, the parallel arms 33 of the based member contain inwardly directed projections which snap over the needle shield when it rotates into the second position and various other structures providing frictional or slight interference engagement can be provided to achieve this result.

For the purpose of illustration needle shield assembly 20 is connected to a hypodermic syringe 56 comprising a syringe barrel 57 having a distal end 58, a proximal end 59 and a circular side wall 61 therebetween defining a chamber 62 for retaining fluid. The distal end of the syringe barrel is connected to the hub so that lumen 25 of the needle cannula is in fluid communication with chamber 62 of the syringe barrel. In this embodiment distal end 58 of the syringe barrel includes an elongate tip having a passageway therethrough which provides the fluid path between the lumen of the cannula and the chamber. The distal end of the syringe barrel also includes a locking luer type collar 63 concentrically surrounding the tip. The luer collar has an array of internal threads which may engage the needle hub to hold it securely to the syringe barrel.

It is also within the purview of the present invention to provide a needle shield assembly wherein the hub is integrally molded with a syringe barrel and the base member is attached to the syringe barrel.

FIG. 7 illustrates an alternative embodiment of the present invention. This embodiment is substantially similar in function to the embodiment of FIGS. 1–6 except for safety indicator means. In particular, alternative needle shield assembly 67 includes needle cannula 21 and elongate needle shield 35 having longitudinal opening 41 as in the embodiment of FIGS. 1–6. In this alternative embodiment, a sleeve 68 having a longitudinal slot 69 is rotatably connected to the exterior of needle shield 35. Sleeve 68 is capable of rotating about said needle shield to an open position wherein longitudinal slot 69 and longitudinal opening 41 are sufficiently aligned to allow the passage of the needle cannula so that the needle shield can be rotated around the base member to a second position where the needle cannula can enter the longitudinal slot of the needle shield. The sleeve can then be rotated to a position, illustrated in FIG. 7, which blocks longitudinal opening 41 of the needle shield. In this embodiment, a larger color segment 71 is deposit on the exterior of needle shield 35. Also, sleeve 68 includes transparent window 70. When sleeve 68 is rotated to cover longitudinal opening 41, as illustrated in FIG. 7, transparent window 70 is positioned over color segment 71 on the needle shield, projecting to the user a bright colored stripe which indicates the needle assembly is securely contained within the needle shield and that the longitudinal opening is covered by the sleeve. The transparent window can be separately made and attached to an aperture in the sleeve, or it can be molded therein by a co-injection process or a co-extrusion process of transparent or translucent materials. The transparent window allows a larger safety indicator without providing another segment on the sleeve for re-exposing the needle.

Figure 8:
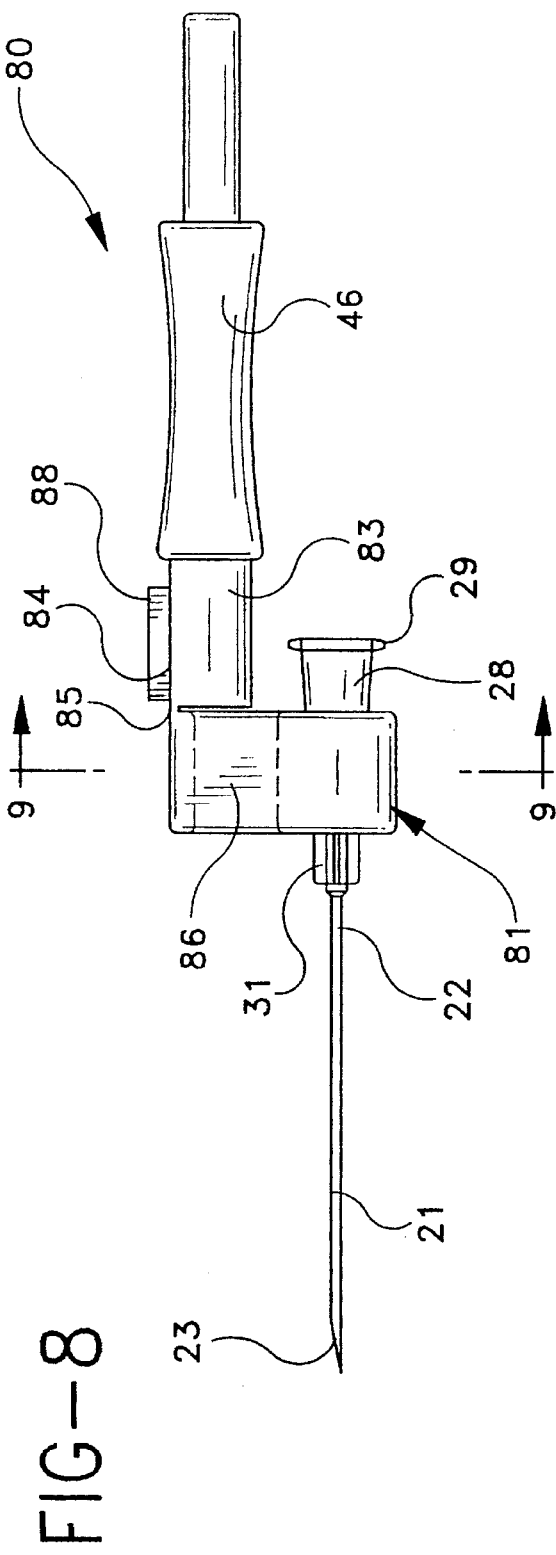
FIG. 8 is a side elevational view of another alternative embodiment of the present invention illustrating a living hinge connection and structure for releasably retaining the needle shield in a needle covering position.
Figure 9:
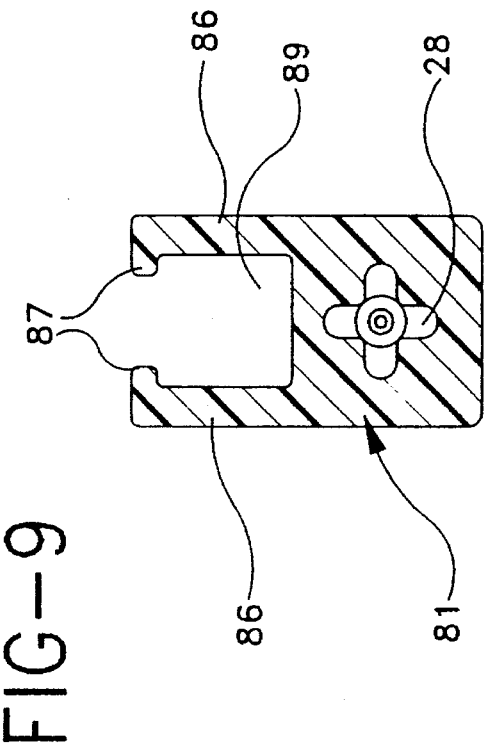
FIG. 9 is a cross-sectional view of the needle shield assembly of FIG. 8 taken along line 9—9.

FIGS. 8–9 illustrate another alternative embodiment of the present invention. Alternative needle assembly 80 functions substantially similarly to the embodiment of FIGS. 1–6 with the exception of the structure hingedly connecting the base member to the elongate needle shield and means for releasably retaining the needle shield in the second needle protecting position. In particular, needle shield assembly 80 includes needle cannula 21 having a proximal end 22, and a distal end 23. A hub 28 having a proximal end 22 for connecting to a medical instrument and a distal end 31 connected to proximal end 32 of the needle cannula. A base member 81 is connected to the hub. An elongate needle shield 83 includes proximal end 84 hingedly connected to base member 81 through living hinge 85. Like the needle shield in the embodiments of FIGS. 1–6, needle shield 83 includes a longitudinal opening therein so that the needle shield is capable of rotating about base member 81 through living hinge 85 from a first position exposing the distal end of the needle cannula, as illustrated in FIG. 8, to a second position wherein the needle cannula is within the longitudinal opening of the needle shield. The embodiment of FIGS. 8–9 also includes means for releasably retaining the needle shield in the second needle protecting position so that a certain amount of force is required to rotate the needle shield out of this position. In this embodiment, means for releasably retaining the needle shield in a second position comprises projections 87 on parallel arms 86 of base member 81 forming a recess 89. Needle shield 83 includes opposed protuberances 88 having a cross-sectional width larger than the distance between projections 87 on the base member.. Accordingly, when the needle shield is rotated into the second needle enclosing position opposing protuberances 88 on the needle shield frictionally engage and pass over projections 87 on the base member, in a snap fit action, to releasably retain the needle shield in a second needle enclosing position. Additional force, over that required to rotate the needle shield on hinge 85, is required to move the needle shield from the second needle enclosing position to a position which exposes the needle cannula because the interference of projections 87 and protuberances 88 must be overcome.

It can be seen that the present invention provides a simple, straight-forward, reliable, easily fabricated needle shield assembly wherein the needle shield can be moved to a needle protecting position using a one-handed procedure and the shield can be selectively locked, through rotation of the sleeve, to prevent further use, or it can be intentionally unlocked to allow a second use of the needle, such as when the needle is being used both for filling the syringe and for delivering the medication. The present invention also provides a clear indication to the user that the shield is safety and securely locked over the needle cannula and that the needle assembly can be disposed of without further risk of needle sticks.

What is claimed is:

1. A needle shield assembly having safety indication features comprising:

a needle cannula having a proximal end, a distal end and a lumen therethrough;

a hub having a proximal end for connecting to a medical instrument and a distal end connected to said proximal end of said needle cannula;

a base member connected to said hub;

an elongate needle shield having a proximal end hingedly connected to said base member, a distal end and a longitudinal axis therebetween, said needle shield having a longitudinal opening therein, said needle shield capable of rotating from a first position exposing at least said distal end of said needle cannula to a second position wherein said needle cannula is within said longitudinal opening of said needle shield;

a sleeve having a longitudinal slot rotatably connected to the exterior of said needle shield, said sleeve capable of rotating about said needle shield to an open position wherein said longitudinal slot and said longitudinal opening are sufficiently aligned to allow passage of said needle cannula so that said needle shield can be rotated from said first position to said second position, said sleeve being rotatable to a position which blocks said longitudinal opening of said needle shield; and color safety indicator means for visually indicating said sleeve is rotated to a position which blocks said longitudinal opening of said needle shield, said color safety indicator means including a color segment on said needle shield which is visible through said sleeve when said sleeve is rotated to a position which blocks said longitudinal opening.

2. The needle shield assembly of claim 1 wherein said color segment is visible through said slot in said sleeve when said sleeve is rotated to a position which blocks said longitudinal opening.

3. The needle shield assembly of claim 1 wherein said sleeve includes an aperture therein and said color segment is visible through said aperture in said sleeve when said sleeve is rotated to a position which blocks said longitudinal opening.

4. The needle assembly of claim 1 wherein said sleeve includes a transparent portion therein sand said color segment is visible through said transparent portion when said sleeve is rotated to a position which blocks said longitudinal opening.

5. The needle assembly of claim 1 wherein said color segment includes a color selected from the group of green, black, blue and white.

6. The needle assembly of claim 1 further including means for limiting rotational movement of said sleeve with respect to said needle shield.

7. The needle assembly of claim 6 when said means for limiting includes a projection on said sleeve and a protuberance on said base member.

8. The needle assembly of claim 1 further including means for releasably retaining said needle shield in said second position.

9. The needle assembly of claim 8 wherein said means for releasably retaining said needle shield in said second position includes a projection on said base member and a recess in said needle shield sized and shaped to frictionally engage said projection on said base member.

10. The needle assembly of claim 1 wherein said hub and said base member are a unitary one-piece structure.

11. The needle assembly of claim 1 wherein said base member and said needle shield are a unitary one-piece plastic structure connected by a living hinge.

12. The needle assembly of claim 1 further including a syringe barrel having a distal end, a proximal end and a circular side wall therebetween defining a chamber for retaining fluid, said distal end of said syringe barrel being connected to said hub so that said lumen of said needle cannula is in fluid communication with said chamber.

13. The needle assembly of claim 12 wherein said hub and said syringe barrel are of a unitary one-piece construction.

14. A needle shield assembly having safety indication features comprising:

a needle cannula having a proximal end, a distal end and a lumen therethrough;

a hub having a proximal end for connecting to a medical instrument and a distal end connected to said proximal end of said needle cannula;

a base member connected to said hub;

an elongate needle shield having a proximal end hingedly connected to said base member, a distal end and a longitudinal axis therebetween, said needle shield having a longitudinal opening therein, said needle shield capable of rotating on said base member from a first position exposing at least said distal end of said needle cannula to a second position wherein said needle cannula is within said longitudinal opening of said needle shield;

means for releasably retaining said needle shield in said second position;

a sleeve having a longitudinal slot rotatably connected to the exterior of said needle shield, said sleeve capable of rotating about said needle shield to an open position wherein said longitudinal slot and said longitudinal opening are sufficiently aligned to allow passage of said needle cannula so that said needle shield can be rotated from said first position to said second position, said sleeve being rotatable to a position which blocks said longitudinal opening of said needle shield;

means for limiting rotational movement of said sleeve with respect to said needle shield; and color safety indicator means on said needle shield for visually indicating said sleeve is rotated to a position which blocks said longitudinal opening of said needle shield, said color safety indicator including a color segment on said needle shield which is visible through said sleeve when said sleeve is rotated to a position which blocks said longitudinal opening.

15. The needle assembly of claim 14 wherein said color segment is visible through said slot in said sleeve when said sleeve is rotated to a position which blocks said longitudinal opening.

16. The needle assembly of claim 14 wherein said means for releasably retaining said needle shield in said second position includes a projection on said needle shield and a recess in said base member sized and shaped to frictionally engage said projection on said needle shield.

17. The needle assembly of claim 14 wherein said means for limiting the rotational movement of the sleeve with respect to said needle shield includes a projection on said sleeve and a protuberance on said needle shield.

* * * * *